United States Patent
Vogtemeir et al.

(10) Patent No.: US 12,138,089 B2
(45) Date of Patent: Nov. 12, 2024

(54) SPECTRAL CT KV RIPPLE DETECTION AND CORRECTION METHOD

(71) Applicant: KONINKLIJKE PHILIPS N.V., Eindhoven (NL)

(72) Inventors: Gereon Vogtemeir, Hamburg (DE); Roger Steadman Booker, Hamburg (DE); Albert Garcia I Tormo, Hamburg (DE); Klaus Jürgen Engel, Lübeck (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 231 days.

(21) Appl. No.: 17/781,429

(22) PCT Filed: Dec. 9, 2020

(86) PCT No.: PCT/EP2020/085148
§ 371 (c)(1),
(2) Date: Jun. 1, 2022

(87) PCT Pub. No.: WO2021/122179
PCT Pub. Date: Jun. 24, 2021

(65) Prior Publication Data
US 2023/0008276 A1   Jan. 12, 2023

(30) Foreign Application Priority Data
Dec. 19, 2019 (EP) .................... 19217968

(51) Int. Cl.
A61B 6/03 (2006.01)
A61B 6/00 (2006.01)
A61B 6/58 (2024.01)
G06T 11/00 (2006.01)

(52) U.S. Cl.
CPC ............ *A61B 6/032* (2013.01); *A61B 6/5205* (2013.01); *A61B 6/58* (2013.01); *G06T 11/005* (2013.01); *G06T 2207/10081* (2013.01)

(58) Field of Classification Search
CPC ......... A61B 6/032; A61B 6/5205; A61B 6/58; A61B 6/482; G06T 11/005; G06T 2207/10081
See application file for complete search history.

(56) References Cited

U.S. PATENT DOCUMENTS

| | | |
|---|---|---|
| 9,113,541 B2 | 8/2015 | Weedon |
| 9,456,790 B2 | 10/2016 | Taguchi |
| 2010/0008558 A1 | 1/2010 | Baeumer |
| 2016/0022243 A1 | 1/2016 | Nakai |
| 2018/0328865 A1* | 11/2018 | Engel .................... A61B 6/482 |

FOREIGN PATENT DOCUMENTS

| | | |
|---|---|---|
| WO | WO2017093520 A1 | 6/2017 |
| WO | WO2019210284 A1 | 10/2019 |

OTHER PUBLICATIONS

PCT International Search Report, International application No. PCT/EP2020/085148, Mar. 2, 2021.

* cited by examiner

*Primary Examiner* — Kiho Kim
(74) *Attorney, Agent, or Firm* — Larry Liberchuk

(57) ABSTRACT

The present invention relates to spectral correction. A spectral correction apparatus is described that is configured to identify a voltage fluctuation in the X-ray tube and to parameterize the high voltage fluctuation to correct the effective X-ray spectrum per individual frame.

11 Claims, 4 Drawing Sheets

SPECTRAL CT KV RIPPLE DETECTION AND CORRECTION METHOD

FIELD OF THE INVENTION

The present invention relates to a spectral correction apparatus, to a spectral correction system, to an X-ray imaging system, to a spectral correction method, as well as to a computer program element and a computer readable medium.

BACKGROUND OF THE INVENTION

For energy resolved X-ray imaging (e.g. Spectral CT), different methods have been developed to measure the energy dependent X-ray projection data. Besides dual layer detectors and direct converter detectors, a promising method for working class spectral is fast voltage switching in the High-Voltage Generator (HVG), namely kV switching. The HVG must enable a fast sequence of two different energy spectra for the X-ray radiation. For the fast switching performance, the capacitive load of the high-voltage cable and the X-ray tube must be minimized. However, lowering the capacitance may yield a higher voltage fluctuation in the X-ray tube. These changes in the voltage up to few percent of the peak voltage would have direct influence on the X-ray spectrum. Since this fluctuation may depend on the operating point of the HVG, the impact on the energy spectra may be different across imaging protocols. WO 2017/093520 A1 describes a method for determining an effective spectrum of an X-ray tube.

SUMMARY OF THE INVENTION

There may be a need to have an improved technique for correcting an effective energy spectra of an X-ray tube.

The object of the present invention is solved by the subject-matter of the independent claims, wherein further embodiments are incorporated in the dependent claims. It should be noted that the following described aspects of the invention apply also for the spectral correction apparatus, the spectral correction system, the X-ray imaging system, the spectral correction method, the computer program element and the computer readable medium.

According to a first aspect of the present invention, there is provided a spectral correction apparatus. The spectral correction apparatus comprises:

an input unit,
a processing unit, and
an output unit.

The input unit is configured to receive a voltage signal generated by a voltage generator that provides electrical input power into an X-ray source of an imaging modality. The processing unit is configured to identify a voltage fluctuation in the voltage signal and to determine a set of parameters describing the voltage fluctuation in the voltage signal, and to use the set of parameters to correct an effective spectrum of the X-ray source per imaging frame. The output unit is configured to output the corrected effective spectrum of the X-ray source per imaging frame.

In other words, an apparatus is provided to receive a voltage signal generated by a voltage generator. Due to the lower capacitive load of the high-voltage cable and the X-ray tube, the voltage signal may have unpredictable fluctuations, e.g., voltage ripples. As the voltage fluctuations are different at every imaging frame, these voltage fluctuations per imaging frame are identified by the apparatus and, instead of storing the complete series, parameterized for further spectral corrections. For example, frequency domain filtering may be used to remove the low-frequency component, e.g., DC signal, of the voltage signal, and to find the high-frequency component, namely voltage fluctuations, at twice the switching frequency plus harmonics, usually beyond 100 kHz. This may be done using standard low-cost integrated circuits, e.g., ADCs, FPGAs, etc. Main parameters for the fluctuations may include fluctuation amplitude, main harmonic frequencies, average values, etc. The main parameters may also include the rise/fall times of the kV switching events. As the fluctuations are parameterized, a simple look-up table may be used to associate the parameters of the voltage fluctuations to a set of spectral correction information for correcting an effective spectrum of the X-ray source per imaging frame. The spectral corrections may also be carried out by a machine learning model, which has been trained to learn the correlation between the parameters of the voltage fluctuations and the spectral correction information.

In an example, the acquisition of the parameters of the voltage fluctuation may be done during regular operation.

In another example, the acquisition of the parameters of the voltage fluctuation may be done at factory.

In a further example, the acquisition of the parameters of the voltage fluctuation may be done during tube conditioning, such as regular tube conditioning, to account for potential drifts over time or environmental conditions.

The proposed apparatus may have at least one of the following advantages:

Spectral correction is performed digitally, i.e. no need to modify any hardware.

Spectral correction may be performed offline. For example, the continuous-time voltage profile may be acquired per imaging frame and the calculation and correction of the effective spectrum per imaging frame is done offline.

Higher kV ripple is accepted without the disadvantage of unknown spectral input signals for the data acquisition per detector frame. This would allow for low-capacitance systems with faster switching times and even for imperfect switching performance and/or voltage overshoot/under shoot situations.

The voltage generator may be simplified by reducing the stringent specification in terms of regulation. This may reduce the requirements of in terms of having the rise/fall times as independent as possible to the operation point of the voltage generator.

The voltage signal may be properly sampled and processed using standard low-cost integrated circuits, such as ADCs and FPGAs.

According to an embodiment of the present invention, the set of parameters comprises at least one of the following parameters per projection: an amplitude of the voltage fluctuation, a main harmonic frequency, and rise/fall times of voltage switching events.

According to an embodiment of the present invention, the set of parameters comprises a set of derived values of parameters across several projections.

For example, for a set of simultaneously acquired images, e.g. the photon count rates for particular energy intervals in the case of an energy separating photon counting detectors, a set of derived values of parameters across these projections is used for correcting the effective spectrum of the X-ray source per imaging frame.

According to an embodiment of the present invention, the input unit is further configured to receive at least one of an anode current of the X-ray source per imaging frame, and an X-ray intensity measurement per imaging frame. The processing unit is further configured to determine the effective spectrum of the X-ray source per imaging frame based on the voltage signal and a total X-ray flux. The total X-ray flux is determined based on at least one of the anode current of the X-ray source per imaging frame and the X-ray intensity measurement per imaging frame.

According to an embodiment of the present invention, the processing unit is configured to apply a pre-defined spectrum-per-voltage calibration table to map the set of parameters of the voltage fluctuation per imaging frame to spectral correction information per imaging frame for correcting the effective spectrum of the X-ray source. The pre-defined spectrum-to-voltage calibration table is configured to store multiple sets of parameters representative of various voltage fluctuations in the voltage signal, each set of parameters being associated with respective spectral correction information for correcting the effective spectrum of the X-ray source per imaging frame. Alternatively or additionally, the processing unit is configured to apply a simulation model to map the set of parameters of the voltage fluctuation per imaging frame to spectral correction information per imaging frame for correcting the effective spectrum of the X-ray source, wherein the simulation model is parameterized based on exemplary pairs of the set of parameters of the voltage fluctuation per imaging frame and the spectral correction information per imaging frame. Alternatively or additionally, the processing unit is configured to apply a machine learning model to map the set of parameters of the voltage fluctuation per imaging frame to spectral correction information per imaging frame for correcting the effective spectrum of the X-ray source, wherein the machine learning model has been trained based on exemplary pairs of the set of parameters of the voltage fluctuation per imaging frame and the spectral correction information per imaging frame.

The pre-defined spectrum-per-voltage calibration table is a look-up table that correlates the spectral correction information with the set of parameters of the voltage fluctuation.

According to an embodiment of the present invention, the voltage signal is obtainable at an operating point of the X-ray source at factory and/or during X-ray source conditioning.

Accordingly, an active measurement of the voltage signal may not be required during regular operation for acquiring parameters of the voltage fluctuation. In this case, the spectra correction may be done based on the operating point of the voltage generator for a given protocol. The acquisition of the parameters of the voltage fluctuation may be done at factory. The parameters of the voltage fluctuation may be acquired during tube conditioning, such as regular tube conditioning, to account for potential drifts over time or environmental conditions.

According to an embodiment of the present invention, the voltage signal comprises a high voltage signal alternating between at least two different voltage levels.

For example, the imaging modality may comprise dual energy CT, also known as spectral CT, that uses two separate X-ray photon energy spectra, allowing the interrogation of materials that have different attenuation properties at different energies.

According to an embodiment of the present invention, the imaging modality comprises at least one of the following: computed tomography (CT), digital X-ray radiography (DXR), and image-guided therapy (IGT).

According to a second aspect of the present invention, there is provided a spectral correction system. The spectral correction system comprises:

a voltage acquisition device, and
a spectral correction apparatus according to the first aspect and any associated example.

The voltage acquisition device is configured to measure a voltage signal generated by a voltage generator that provides electrical input power into an X-ray source of an imaging modality. The spectral correction apparatus is configured to output a corrected effective spectrum of the X-ray source per imaging frame.

According to an embodiment of the present invention, the spectral correction system further comprising at least one of:

an anode current acquisition device configured to measure an anode current of the X-ray source per imaging frame, and
an X-ray intensity acquisition device configured to measure an X-ray intensity measurement per imaging frame.

The apparatus is configured to determine an effective spectrum of the X-ray source per imaging frame based on the voltage signal and a total X-ray flux. The total X-ray flux is determined based on at least one of the anode current of the X-ray source per imaging frame and the X-ray intensity measurement per imaging frame.

The X-ray intensity acquisition device measuring the time-resolved X-ray intensity may replace a state of the art X-ray flux reference detector that measures the integral intensity per frame. Alternatively, the X-ray intensity acquisition device may be introduced complementary to the reference detector.

According to a third aspect of the present invention, there is provided an X-ray imaging system, comprising;

an image acquisition apparatus,
a spectra correction system according to the second aspect and any associated example, and
a reconstruction device.

The image acquisition apparatus is configured to scan an object of interest to generate X-ray data comprising one or more image slices, each representative of a certain thickness of the object being scanned in a certain angle of projection. The spectral correction system is configured to output a corrected effective spectrum of an X-ray source per imaging frame of the X-ray imaging system. The reconstruction apparatus is configured to apply the corrected effective spectrum of the X-ray source per imaging frame for image reconstruction.

As used herein, the term "X-ray image data" may be a single "X-ray attenuation" image. The term "X-ray image data" may also refer to dual energy data (attenuation values at two energy spectra) or multi energy data (attenuation values at more than two energy spectra), which can be used to reconstruct numerous image types, such as: weighted average images (simulating single energy spectra);

virtual monoenergetic images (attenuation at a single photon energy rather than a spectrum);
material decomposition images (mapping or removing substances of known attenuation characteristics, such as iodine, calcium, or uric acid)
virtual non-contrast images (iodine removed);
iodine concentration (iodine maps);
calcium suppression (calcium removed);
uric acid suppression (uric acid removed);
electron density maps; and
effective atomic number ($Z_{eff}$) maps.

In an example, the reconstruction apparatus and the spectral correction apparatus may be two different apparatuses.

In an example, the reconstruction apparatus and the spectral correction apparatus may be the same apparatus. In other words, the reconstruction apparatus may be configured to have the spectral correction function.

According to a fourth aspect of the present invention, there is provided a spectral correction method. The method comprises:

receiving a voltage signal generated by a voltage generator that provides electrical input power into an X-ray source of an imaging modality;

determining a voltage fluctuation in the voltage signal and a set of parameters describing the voltage fluctuation in the voltage signal;

using the set of parameters to correct an effective spectrum of the X-ray source per imaging frame; and outputting the corrected effective spectrum of the X-ray source per imaging frame.

In an example, the set of parameters may comprise at least one of the following parameters per projection: an amplitude of the voltage fluctuation, a main harmonic frequency, and rise/fall times of voltage switching events.

In an example, the set of parameters may comprise a set of derived values of parameters across several projections.

In an example, step a) may further comprise receiving at least one of an anode current of the X-ray source per imaging frame, and an X-ray intensity measurement per imaging frame. Step c) further comprises determining the effective spectrum of the X-ray source per imaging frame based on the voltage signal and a total X-ray flux. The total X-ray flux is determined based on at least one of the anode current of the X-ray source per imaging frame and the X-ray intensity measurement per imaging frame.

In an example, step c) may further comprise applying a pre-defined spectrum-per-voltage calibration table to map the set of parameters of the voltage fluctuation per imaging frame to spectral correction information per imaging frame for correcting the effective spectrum of the X-ray source. The pre-defined spectrum-to-voltage calibration table stores multiple sets of parameters representative of various voltage fluctuations in the voltage signal, each set of parameters being associated with respective spectral correction information for correcting the effective spectrum of the X-ray source per imaging frame.

In an example, step c) may further comprise applying a simulation model to map the set of parameters of the voltage fluctuation per imaging frame to spectral correction information per imaging frame for correcting the effective spectrum of the X-ray source. The simulation model is parameterized based on exemplary pairs of the set of parameters of the voltage fluctuation per imaging frame and the spectral correction information per imaging frame.

In an example, step c) may further comprise applying a machine learning model to map the set of parameters of the voltage fluctuation per imaging frame to spectral correction information per imaging frame for correcting the effective spectrum of the X-ray source, wherein the machine learning model has been trained based on exemplary pairs of the set of parameters of the voltage fluctuation per imaging frame and the spectral correction information per imaging frame In an example, the voltage signal may be obtainable at an operating point of the X-ray source at factory and/or during X-ray source conditioning.

In an example, the voltage signal may comprise a high voltage signal alternating between at least two different voltage levels.

In an example, the imaging modality may comprise at least one of the following: CT, DXR, and IGT.

According to an embodiment of the present invention, the method further comprises the step of applying the corrected effective spectrum of the X-ray source per imaging frame for image reconstruction.

In an example, the method further comprises outputting data representative of the result of image reconstruction.

According to another aspect of the present invention, there is provided a computer program element controlling apparatus as previously described which, if the computer program element is executed by a processing unit, is adapted to perform the method steps as previously described.

According to another aspect of the present invention, there is provided a computer readable medium having stored computer element as previously described.

Advantageously, the benefits provided by any of the above aspects and examples equally apply to all of the other aspects and examples and vice versa.

As used herein, the term "voltage fluctuation" may refer to any change and deviation of the voltage from the defined voltage setting with calibrated X-ray spectrum, such as drift, regular frequency components, and unpredictable influences. Various influencing factors may be taken into account for the spectral correction.

As used herein, the term "imaging frame" may refer to a single image from an analogue or digital series.

As used herein, the term "projection" may refer to a one-dimensional or two-dimensional attenuation profile. There is one projection for each angular position of the detector during data collection and a complete set of projections for each tomogram to be reconstructed.

As used herein, the term "unit" may refer to, be part of, or include an Application Specific Integrated Circuit (ASIC), an electronic circuit, a processor (shared, dedicated, or group) and/or memory (shared, dedicated, or group) that execute one or more software or firmware programs, a combinational logical circuit, and/or other suitable components that provide the described functionality.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Typical operating frequencies for the HVG are in the range of 10 to 100 kHz; nevertheless, depending on the control technique used in the HVG, some low-frequency components may be present in the output voltage as well. The lower frequency contribution would lead to different effective voltages per detector frame time in case the switching frequency and the acquisition frequency are not synchronized. Consequently the effective X-ray spectrum per detector frame time would differ from frame to frame.

The solution to synchronize acquisition frequency and transformer switching frequency is not a preferred solution, as the frame time should be synchronized to the gantry angular position, which would depend on the rotation speed and timing. A synchronization of the generator switching frequency to the angular speed is also not preferable since, in order to maximize the efficiency of the HVG, the HVG operated at a variable frequency given by the HVG's components (whose tolerance may be beyond 10%) and instantaneous power consumption.

Figure 1:
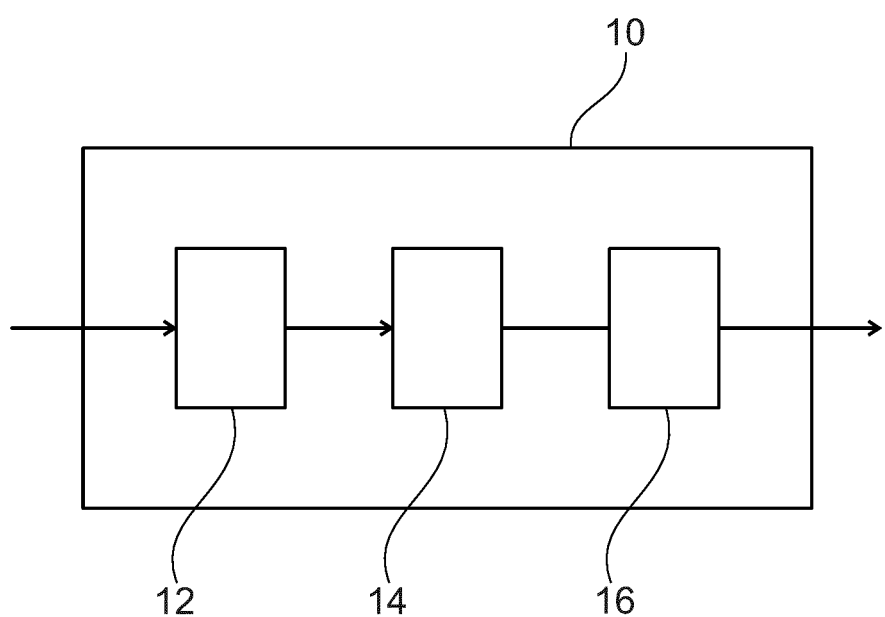
FIG. 1 schematically shows a spectral correction apparatus according to some embodiments of the present disclosure.

Towards this end, FIG. 1 shows a spectral correction apparatus 10 according to some embodiments of the present disclosure.

The apparatus 10 may be applicable to spectral systems and non-spectral systems. In a spectral system, at least two measurements per spatial projection through an object are acquired. Each value is in an individual way dependent on the effective spectrum, which may be considered as a spectrum integral with a particular weighting function. In a non-spectral system, only a single integral spectrum is determined per spatial projection through an object in a single value.

The spectral correction apparatus 10 comprises an input unit 12, a processing unit 14, and an output unit 16. The input unit 12 is configured to receive a voltage signal generated by a voltage generator that provides electrical input power into an X-ray source of an imaging modality. For example, the control of the voltage generator may include measuring the voltage signal at the output of the voltage generator, by means of a voltage divider. A low-voltage signal representing the voltage of the X-ray source is therefore available. These amplitude variations have a high-frequency component and a low-frequency component. The high-frequency component is representative of a voltage fluctuation, which is at twice the switching frequency plus harmonics, usually beyond 100 kHz. The low-frequency component is representative of chattering, which could be at any frequency down to DC. These two frequency components may be properly sampled and processed using standard low-cost integrated circuits.

In an example, the voltage signal may be acquired during regular operation.

However, for acquiring a set of parameters of the voltage fluctuations, an active measurement of the voltage signal is not required during regular operation. For example, the voltage signal may be measured at factory for acquiring the set of parameters of the voltage fluctuations. For example, the voltage signal may be measured during tube conditioning for acquiring the set of parameters of the voltage fluctuations to account for potential drifts over time or environmental conditions.

In an example, the imaging modality comprises at least one of the following: CT, digital X-ray radiography (DXR), and image-guided therapy (IGT).

The processing unit 14 is configured to identify a voltage fluctuation in the voltage signal and to determine a set of parameters describing the voltage fluctuation in the voltage signal, and to use the set of parameters to correct an effective spectrum of the X-ray source per imaging frame. In other words, each projection may be analyzed by the spectral correction apparatus and parameterized for further corrections.

In an example, the set of parameters comprises at least one of the following parameters per projection: an amplitude of the voltage fluctuation, a main harmonic frequency, and rise/fall times of voltage switching events.

In an example, the voltage signal comprises a high voltage signal alternating between at least two different voltage levels. In other words, the X-ray image data may be spectral X-ray image data with a broadband X-ray source operating with spectral sensitive X-ray detector. For example, in CT, materials having different elemental compositions can be represented by identical pixel values on a CT image, depending on the mass density of the material. Thus, the differentiation and classification of different tissue types and contrast agents can be extremely challenging. In dual-energy CT, an additional attenuation measurement is obtained with a second X-ray spectrum (i.e., a second "energy"), allowing the differentiation of multiple materials. Alternatively, this allows quantification of the mass density of two or three materials in a mixture with known elemental composition. In the use of energy-resolving, photon-counting detectors for CT imaging, X-ray image data may be acquired in multiple energy bins, which is expected to further improve the signal-to-noise ratio for material-specific imaging. Accordingly, the X-ray image data may comprise a set of simultaneously acquired images. In this case, the set of parameters may comprise a set of derived values of parameters of the voltage fluctuation across several projections with known tube conditions. For example, the kV signals for a kV switching protocol may have a pair of parameters representative of the average performance at e.g. low peak kilovoltage (kVp) and high kVp.

In an example, the effective spectrum may be obtained from an external spectrum processing device.

In an example, the input unit 12 may be further configured to receive an anode current of the X-ray source per imaging frame. Alternatively or additionally, the input unit is further configured to receive an X-ray intensity measurement per imaging frame. The processing unit 14 is further configured to determine the effective spectrum of the X-ray source per imaging frame based on the voltage signal and a total X-ray flux. The total X-ray flux is determined based on at least one of the anode current of the X-ray source per imaging frame and the X-ray intensity measurement per imaging frame.

The X-ray spectrum as a histogram versus photon energy E is a function of the tube voltage V(t) and the anode current I(t), which is built by the electrons collected by the anode, both as a function of time t. The calculation of an X-ray flux spectrum is in a function $$\psi(E,V,I)=I(t)\cdot\psi(E,V(t))$$

where $\psi(E,V)$ provides the number of photons at energy E emitted into a particular direction in units of photons per mA per s per solid angle. Given the case that the time dependencies V(t) and I(t) are known (i.e. measured), an effective spectrum N(E), given in units of photons per solid angle, can be calculated as an integral (or sum respectively) over time:

$$N(E)=\int I(t)\cdot\psi(E,V(t))\cdot dt$$

In case that I(t) and V(t) are measured directly, the effective spectrum can be derived directly from the integral. In case that instead of I(t) the X-ray flux S(t) is measured from a time resolving reference detector, an intermediate step needs to be taken, i.e. a table representing the average flux $\bar{S}(\bar{V},I)$ for various $\bar{V}$ is taken in calibration measurements. From this table, the function I(t) is derived by calculating $$I(t) = \bar{I} \cdot \frac{s(t)}{\bar{S}(V(t),\bar{I})}$$

There are various methods for correcting the effective spectrum of the X-ray source per imaging frame with the set of parameters of the voltage fluctuation.

In an example, machine learning may be used. A machine learning model may be trained for learning the correlation between the set of parameters of the voltage fluctuation and the spectral correction information for spectral corrections.

In an example, a simulation model may be applied to map the set of parameters of the voltage fluctuation per imaging frame to spectral correction information per imaging frame for correcting the effective spectrum of the X-ray source. The simulation model is parameterized based on exemplary pairs of the set of parameters of the voltage fluctuation per imaging frame and the spectral correction information per imaging frame.

In an example, the processing unit 14 may be further configured to apply a pre-defined spectrum-per-voltage calibration table to map the set of parameters of the voltage fluctuation per imaging frame to spectral correction information per imaging frame for correcting the effective spectrum of the X-ray source. The pre-defined spectrum-to-voltage calibration table may be configured to store multiple sets of parameters representative of various voltage fluctuations in the voltage signal, each set of parameters being associated with respective spectral correction information for correcting the effective spectrum of the X-ray source per imaging frame. The predefined spectrum-per-voltage calibration table may associate e.g. one or more of fluctuation amplitude, main harmonic frequencies, rise/fall times of the kV switching events, to a set of spectral correction information in units of photons per solid angle. The predefined spectrum-per-voltage calibration table may be derived from previously measured results, e.g., empirical findings of laboratory experiments. Interpolation may be used for constructing new data points within the range of a discrete set of the previously measured results.

The output unit 16 is configured to output the corrected effective spectrum of the X-ray source per imaging frame, e.g., for image reconstruction.

In an example, the apparatus may be used in medical X-ray imaging or image display. For example, the apparatus may be used in C-arm or CT X-ray systems utilizing spectral information within the X-rays.

In an example, the apparatus may be used in non-medical X-ray imaging or image display. For example, the apparatus may be used in non-destructive testing systems or in screening systems, e.g., airport luggage screening systems.

In an example, the apparatus may be used in tomosynthesis imaging or image display.

Figure 2:
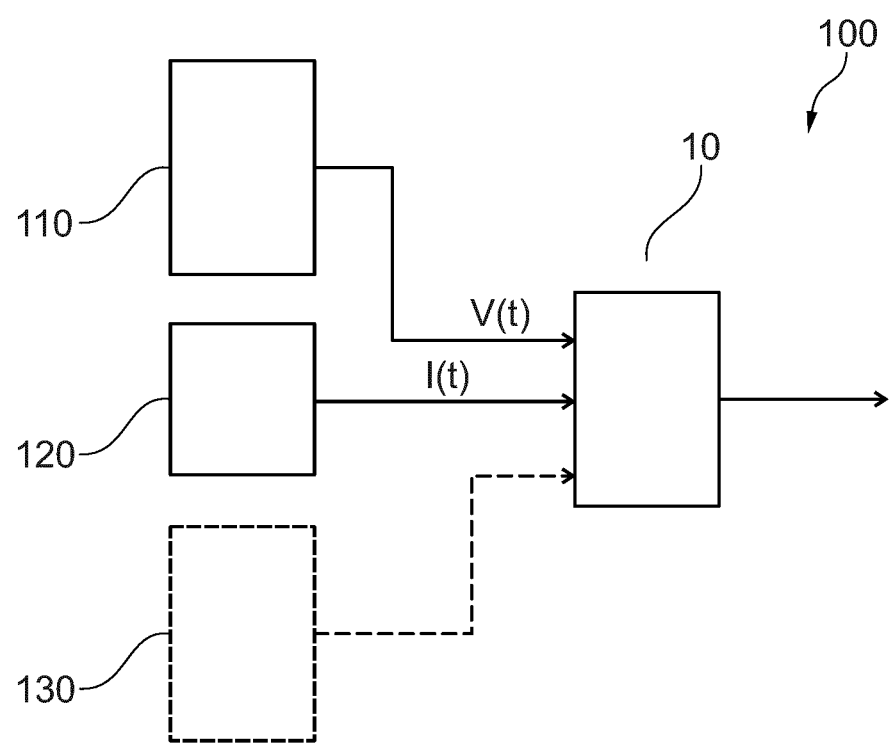
FIG. 2 schematically shows a spectral correction system according to some embodiments of the present disclosure.

FIG. 2 shows a spectral correction system 100 according to some embodiments of the present disclosure. The spectral correction system 100 comprises a voltage acquisition device 110 and a spectral correction apparatus 10 according to the apparatus described with respect to FIG. 1.

The voltage acquisition device 110 is configured to measure a voltage signal generated by a voltage generator that provides electrical input power into an X-ray source of an imaging modality. For example, the voltage acquisition device 110 may measure the voltage signal at the output of the voltage generator, by means of a voltage divider.

The spectral correction apparatus is configured to output a corrected effective spectrum of the X-ray source per imaging frame based on the voltage signal.

Optionally, the spectral correction system 100 may further comprise an anode current acquisition device 120 configured to measure an anode current of the X-ray source per imaging frame. As a further option (shown as dotted lines), the spectral correction system 100 may further comprise an X-ray intensity acquisition device 130 configured to measure an X-ray intensity measurement per imaging frame. The spectral correction apparatus is configured to determine an effective spectrum of the X-ray source per imaging frame based on the voltage signal and a total X-ray flux. The total X-ray flux is determined based on at least one of the anode current of the X-ray source per imaging frame and the X-ray intensity measurement per imaging frame.

In an example, the X-ray intensity acquisition device 130 measuring the time-resolved X-ray intensity may replace a state of the art X-ray flux reference detector that measures the integral intensity per frame. Alternatively, the X-ray intensity acquisition device 130 may be introduced complementary to the reference detector.

Figure 3:
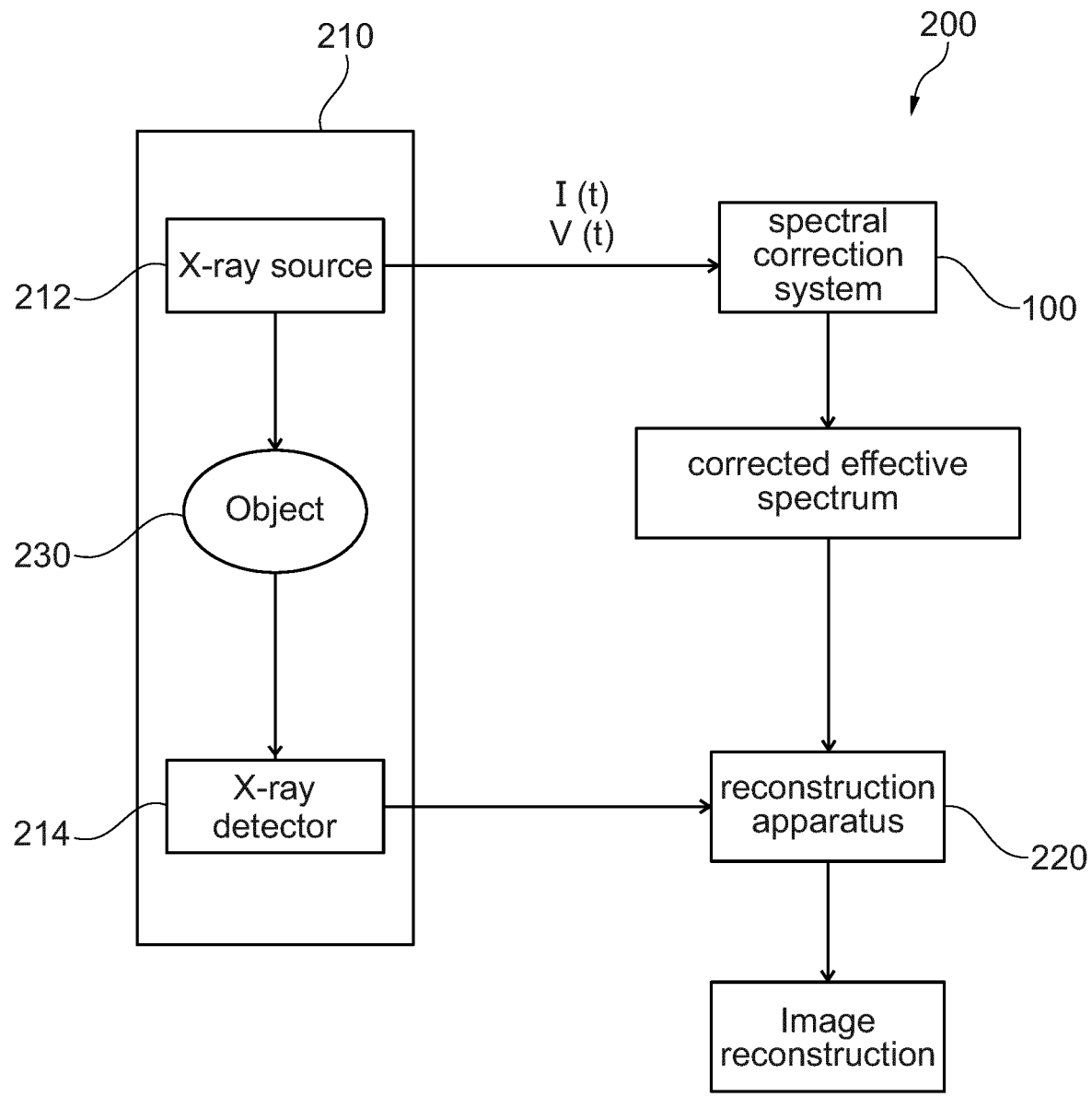
FIG. 3 schematically shows an X-ray imaging system according to some embodiments of the present disclosure.

FIG. 3 shows an X-ray imaging system 200 according to some embodiments of the present disclosure. Examples of the X-ray imaging system include, but are not limited to, a C-arm system, a CT system, a DXR system, and an IGT system.

The X-ray imaging system 200 comprises an image acquisition apparatus 210, a spectral correction system 100 according to the spectral correction system described with respect to FIG. 2, and a reconstruction apparatus 220.

The image acquisition apparatus 210 comprises an X-ray detector 214 opposing the X-ray source 212. The image acquisition apparatus 210 is configured to scan an object of interest 230 to generate X-ray image data, namely raw-image, comprising one or more image slices, each representative of a certain thickness of the object being scanned in a certain angle of projection.

The spectral correction system 100 may be configured to obtain a voltage signal generated by a voltage generator that provides electrical input power into the X-ray source. The spectral correction apparatus 100 may be further configured to at least one of the anode current of the X-ray source per imaging frame and the X-ray intensity measurement per imaging frame. The spectral correction system 100 is configured to output a corrected effective spectrum of the X-ray source per imaging frame.

The reconstruction apparatus 220 is configured to apply the corrected effective spectrum of the X-ray source per imaging frame for image reconstruction.

Figure 4:
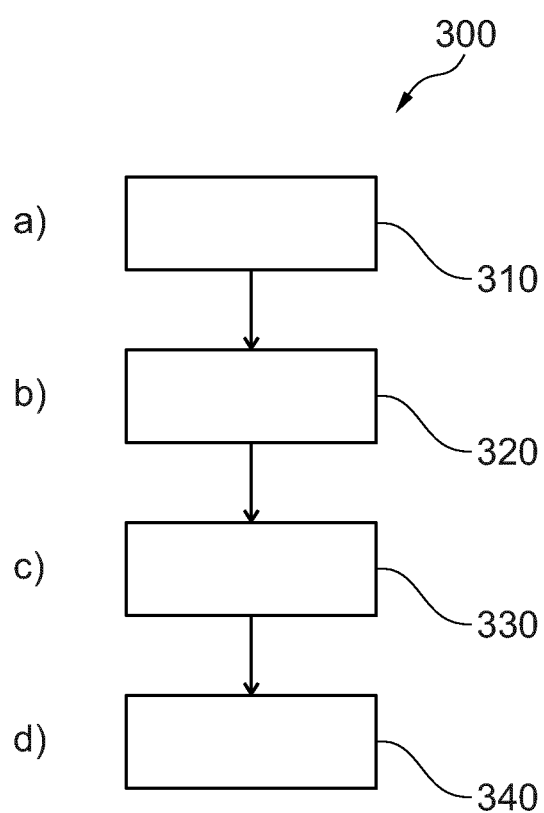
FIG. 4 shows a spectral correction method according to some embodiments of the present invention.

FIG. 4 shows a spectral correction method 300 according to some embodiments of the present disclosure. The method comprises:

In step 310, i.e. step a), a voltage signal generated by a voltage generator is received that provides electrical input power into an X-ray source of an imaging modality.

Optionally, the voltage signal may be obtainable at an operating point of the X-ray source at factory and/or during X-ray source conditioning.

Optionally, the voltage signal may comprise a high voltage signal alternating between at least two different voltage levels.

Optionally, step a) may further comprise receiving at least one of an anode current of the X-ray source per imaging frame, and an X-ray intensity measurement per imaging frame. Step c) further comprises determining the effective spectrum of the X-ray source per imaging frame based on the voltage signal and a total X-ray flux. The total X-ray flux is determined based on at least one of the anode current of the X-ray source per imaging frame and the X-ray intensity measurement per imaging frame.

Optionally, the imaging modality may comprise at least one of the following: CT, DXR, and IGT.

In step 320, i.e. step b), a voltage fluctuation in the voltage signal and a set of parameters describing the voltage fluctuation in the voltage signal are determined. As an example, frequency domain filtering may be used to remove the low-frequency component, e.g., DC signal, of the voltage signal, and to find the high-frequency component, namely voltage fluctuations, at twice the switching frequency plus harmonics, usually beyond 100 kHz. This may be done using standard low-cost integrated circuits, e.g., ADCs, FPGAs, etc. In step 330, i.e. step c), the set of parameters is used to correct an effective spectrum of the X-ray source per imaging frame.

Optionally, step c) may further comprise applying a pre-defined spectrum-per-voltage calibration table to map the set of parameters of the voltage fluctuation per imaging frame to spectral correction information per imaging frame for correcting the effective spectrum of the X-ray source. The pre-defined spectrum-to-voltage calibration table stores multiple sets of parameters representative of various voltage fluctuations in the voltage signal, each set of parameters being associated with respective spectral correction information for correcting the effective spectrum of the X-ray source per imaging frame.

Optionally, step c) may further comprise applying a simulation model to map the set of parameters of the voltage fluctuation per imaging frame to spectral correction information per imaging frame for correcting the effective spectrum of the X-ray source. The simulation model is parameterized based on exemplary pairs of the set of parameters of the voltage fluctuation per imaging frame and the spectral correction information per imaging frame; and/or Optionally, step c) may further comprise applying a machine learning model to map the set of parameters of the voltage fluctuation per imaging frame to spectral correction information per imaging frame for correcting the effective spectrum of the X-ray source. The machine-learning model has been trained based on exemplary pairs of the set of parameters of the voltage fluctuation per imaging frame and the spectral correction information per imaging frame.

In step 340, i.e. step d), the corrected effective spectrum of the X-ray source per imaging frame is output.

Optionally, the method 300 may further comprise the step of applying the corrected effective spectrum of the X-ray source per imaging frame for image reconstruction.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A spectral correction apparatus, comprising:
a memory that stores a plurality of instructions; and
processor circuitry that couples to the memory and is configured to execute the plurality of instructions to:
receive a voltage signal generated by a voltage generator that provides electrical input power into an X-ray source of an imaging modality;
identify a voltage fluctuation in the voltage signal;
determine a set of parameters describing the voltage fluctuation in the voltage signal;

correct an effective spectrum of the X-ray source per imaging frame using the set of parameters; and output the corrected effective spectrum of the X-ray source per imaging frame.

2. The apparatus according to claim 1, wherein the set of parameters comprises at least one of the following parameters per projection:

an amplitude of the voltage fluctuation;

a main harmonic frequency; and rise/fall times of voltage switching events.

3. The apparatus according to claim 2, wherein the set of parameters comprises a set of derived values of parameters across several projections.

4. The apparatus according to claim 1, wherein the processor circuitry is further configured to receive at least one of:

an anode current of the X-ray source per imaging frame; and an X-ray intensity measurement per imaging frame; and wherein the processor circuitry is further configured to determine the effective spectrum of the X-ray source per imaging frame based on the voltage signal and a total X-ray flux, wherein the total X-ray flux is determined based on at least one of the anode current of the X-ray source per imaging frame and the X-ray intensity measurement per imaging frame.

5. The apparatus according to claim 1, wherein the processor circuitry is further configured to:

i) apply a pre-defined spectrum-per-voltage calibration table to map the set of parameters of the voltage fluctuation per imaging frame to spectral correction information per imaging frame for correcting the effective spectrum of the X-ray source; and wherein the pre-defined spectrum-to-voltage calibration table is configured to store multiple sets of parameters representative of various voltage fluctuations in the voltage signal, each set of parameters being associated with respective spectral correction information for correcting the effective spectrum of the X-ray source per imaging frame;

ii) apply a simulation model to map the set of parameters of the voltage fluctuation per imaging frame to spectral correction information per imaging frame for correcting the effective spectrum of the X-ray source, wherein the simulation model is parametrized based on exemplary pairs of the set of parameters of the voltage fluctuation per imaging frame and the spectral correction information per imaging frame; and/or iii) apply a machine learning model to map the set of parameters of the voltage fluctuation per imaging frame to spectral correction information per imaging frame for correcting the effective spectrum of the X-ray source, wherein the machine learning model has been trained based on exemplary pairs of the set of parameters of the voltage fluctuation per imaging frame and the spectral correction information per imaging frame.

6. The apparatus according to claim 1, wherein the voltage signal is obtainable at an operating point of the X-ray source and/or during X-ray source conditioning.

7. The apparatus according to claim 1, wherein the voltage signal comprises a high voltage signal alternating between at least two different voltage levels.

8. The apparatus according to claim 1, wherein the imaging modality comprises at least one of the following:

computed tomography (CT);

digital X-ray radiography (DXR); and image-guided therapy (IGT).

9. A spectral correction method, comprising:

receiving a voltage signal generated by a voltage generator that provides electrical input power into an X-ray source of an imaging modality;

determining a voltage fluctuation in the voltage signal and a set of parameters describing the voltage fluctuation in the voltage signal;

using the set of parameters to correct an effective spectrum of the X-ray source per imaging frame; and outputting the corrected effective spectrum of the X-ray source per imaging frame.

10. The method according to claim 9, further comprising:

applying the corrected effective spectrum of the X-ray source per imaging frame for image reconstruction.

11. A non-transitory computer-readable medium for storing executable instructions, which cause a spectral correction method to be performed, the method comprising:

receiving a voltage signal generated by a voltage generator that provides electrical input power into an X-ray source of an imaging modality;

determining a voltage fluctuation in the voltage signal and a set of parameters describing the voltage fluctuation in the voltage signal;

using the set of parameters to correct an effective spectrum of the X-ray source per imaging frame; and outputting the corrected effective spectrum of the X-ray source per imaging frame.

* * * * *